US006576466B2

(12) United States Patent
Jungfer et al.

(10) Patent No.: US 6,576,466 B2
(45) Date of Patent: Jun. 10, 2003

(54) TUMORICIDAL T LYMPHOCYTES

(75) Inventors: Herbert Jungfer, Starnberg (DE); Heinrich Barchet, Bernried (DE); Winfred Albert, Eberfing (DE); Ulrich Weidle, München (DE)

(73) Assignee: Albert Winfried, Weilheim (DE)

( * ) Notice: Subject to any disclaimer, the term of this patent is extended or adjusted under 35 U.S.C. 154(b) by 0 days.

(21) Appl. No.: 08/513,865

(22) PCT Filed: Mar. 26, 1994

(86) PCT No.: PCT/EP94/00960
§ 371 (c)(1),
(2), (4) Date: Dec. 4, 1995

(87) PCT Pub. No.: WO94/23014
PCT Pub. Date: Oct. 13, 1994

(65) Prior Publication Data
US 2002/0039569 A1 Apr. 4, 2002

(30) Foreign Application Priority Data
Mar. 31, 1993 (DE) .......................................... 43 10 229

(51) Int. Cl.$^7$ .......................... C12N 5/06; C12N 5/08; A01N 63/00; A61K 35/26
(52) U.S. Cl. ................. 435/372.3; 435/372; 435/372.2; 435/375; 435/377; 435/347; 424/53.71; 424/520
(58) Field of Search ................ 424/520, 85.2; 435/7.24, 325, 372.5, 373, 375, 377, 347; 530/389.6; 935/101

(56) References Cited

FOREIGN PATENT DOCUMENTS

| DE | 39 23 848 | 7/1989 |
| EP | A 0 203 403 | 4/1987 |
| EP | 0 415 666 A1 | 8/1990 |
| WO | WO 90/10059 | 7/1990 |

OTHER PUBLICATIONS

De Vries et al. The Journal of Immunology. Jan. 1984. vol. 132, No. 1, pp. 510–519.*
Paul, in Fundamental Immunology, Third Edition, Raven Press, Chapter 32, p. 1158, 1993.*
Cesano et al., Cancer Research, 56:3021–3029, 1996.*
Bachmann et al., Current Opinion in Immunology, 6:320–326, 1994.*
Lancki et al., Biotherapy, 5:71–81, 1992.*
Ballas, Z.K., and Rasmussen, W., "Lymphokine–Activated Killer (LAK) Cells, IV. Characterization of Murine LAK Effector Subpopulations", *The Journal of Immunology*, 144:386–395 (1990).
Chen, B.P., et al., "Selective Lysis of Target Cells by Interleukin–2–Expanded Peripheral Blood Mononuclear Leukocyte Clones", *Cellular Immunology*, 118:458–469 (1989).

Darrow, T.L., et al., "The role of HLA class I antigens in recognition of melanoma cells by tumor–specific cytotoxic T lymphocytes", *The Journal of Immunology*, 142:3329–3335 (1989).
Degiovanni, G., et al., "Antigenic heterogeneity of a human melanoma tumor detected by autologous CTL clones", *Eur. J. Immunol.*, 18:671–676 (1988).
Fossati, G., et al., "Proliferative and/or cytotoxic activity of lymphocyte clones to autologous human melanoma", *Int. J. Cancer*, 42:239–245 (1988).
Fox, B.A., and Rosenberg, S.A., "Heterogeneous lymphokine–activated killer cell precursor populations", *Cancer Immunol. Immunother.*, 29:155–166 (1989).
Notter, M., and Schirrmacher, V., "Tumor–specific T–cell clones recognize different protein determinants of autologous human malignant melanoma cells", *Int. J. Cancer*, 45:834–841 (1990).
Rosenberg, S.A., "Immunotherapy of cancer using interleukin 2: current status and future prospects", *Immunology Today*, vol. 9, No. 2:58–62 (1988).
Thiele, D.L., and Lipsky, P.E., "The role of cell surface recognition structures in the initiation of MHC–unrestricted "promiscuous" killing by T cells", *Immunology Today*, vol. 10, No. 11:375–381 (1989).
Thiele, D.L., and Lipsky, P.E., "Leu–Leu–Ome Sensitivity of human activated killer cells: delineation of a distinct class of cytotoxic T lymphocytes capable of lysing tumor targets", *The Journal of Immunology*, 137:1399–1406 (1986).
Woelfel, T., et al., "Lysis of human melanoma cells by autologous cytolytic T cell clones", *J. Exp. Med.*, 170:797–810 (1989).
Yssel, H., et al., "A clones human T cell line cytotoxic for autologous and allogeneic B lymphoma cells", *J. Exp. Med.*, 160:239–254 (1984).
Melief et al, *Advances in Cancer Research*, vol. 58, pp. 143–175.
Thiele et al, *Proc. Natl. Acad. Sci. USA*, vol. 87, pp. 88–87 Jan. 1990.
Ljunggren et al, *Immunology Today*, vol. 11, No. 7, 1990.
Borden et al, *Cancer*, Feb. 1 Supplement 1990, vol. 65, pp. 800–814.
Rosenberg, *Cancer Treatment Reviews*, (1989) 16 (Supplement A), pp. 115–121.
Thiele et al, *The Journal of Immunology*, vol. 136, No. 3, Feb 1, 1986, pp. 1038–1048.

* cited by examiner

Primary Examiner—Irene Marx
Assistant Examiner—Vera Afremova
(74) Attorney, Agent, or Firm—Arent Fox Kintner Plotkin Kahn, PLLC

(57) ABSTRACT

The present invention concerns a mammalian cell line which when co-cultured with lymphocytes during which allogenic stimulation is avoided activates lymphocytes fo form tumoricidal cells, a process for the production of tumoricidal T lymphocytes by co-culturing lymphocytes with this cell line, the tumoricidal T lymphocytes obtained by means of this process and the use of the cells according to the present invention for the production of a therapeutic agent which can be used in tumour therapy.

12 Claims, 2 Drawing Sheets

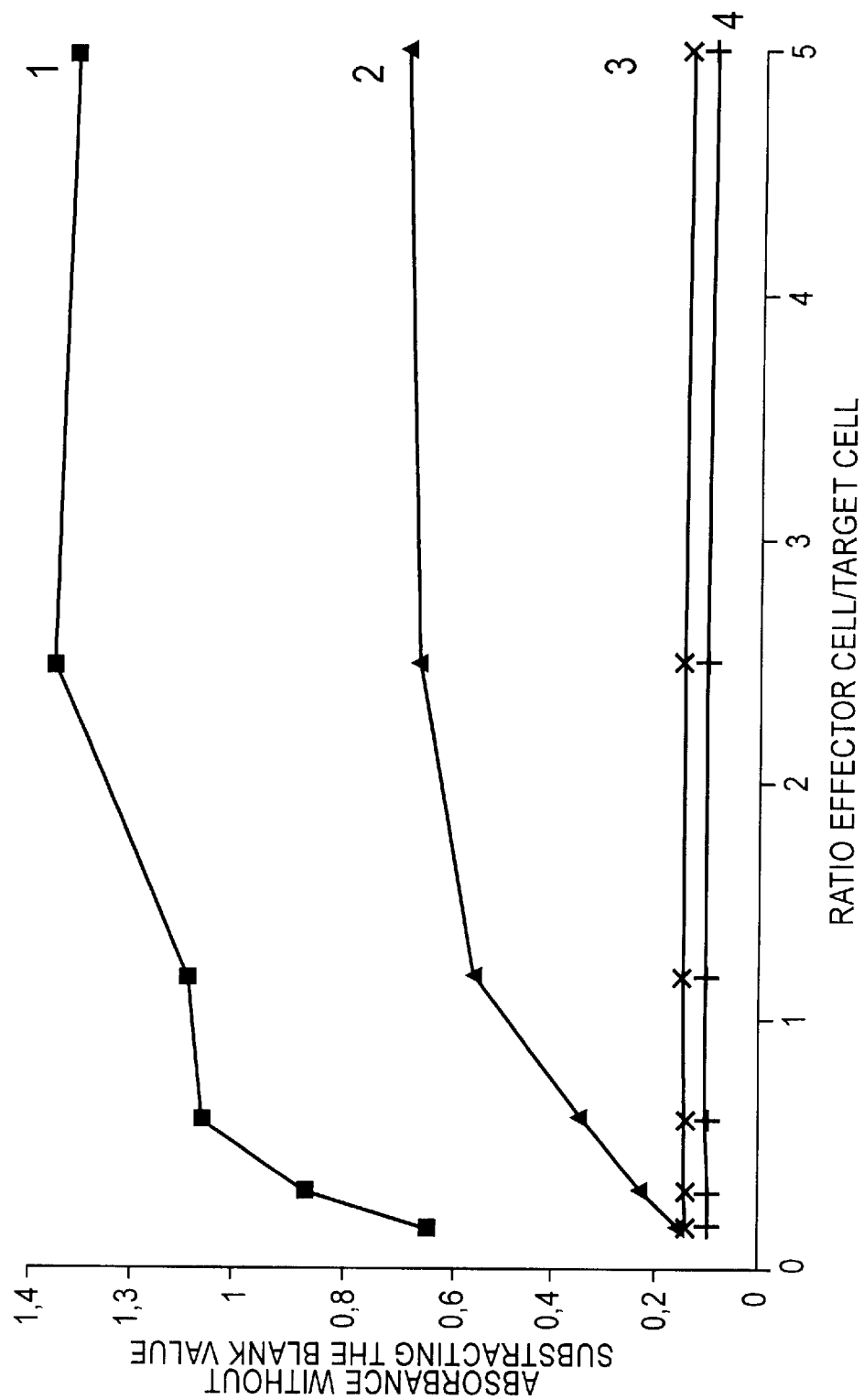

TUMORICIDAL T LYMPHOCYTES

BACKGROUND OF THE INVENTION

The present invention concerns a mammalian cell line and its active fragments which when it is co-cultured with lymphocytes during which allogenic stimulation is avoided, activate lymphocytes to form tumoricidal T cells a process for the production of tumoricidal T lymphocytes by co-culturing lymphocytes with such cell lines or with active fragments thereof, the tumoricidal T lymphocytes obtainable by this process as well as the use of these T lymphocytes for the production of a therapeutic agent which can be used in tumour therapy.

The cellular immune defence plays an important role in the elimination of pathologically changed endogenic cells such as e.g. cells infected by viruses or tumour cells. In this process cytotoxically active T lymphocytes recognize the changed endogenic cells on the basis of surface antigens. These surface antigens are usually protein fragments which are formed by the cells and are present on the cell surface bound to surface receptors of the so-called major-histocompatibility complex (MHC) (Zinkernagel et al., Nature 248 (1974), 701–702 and Babbit et al., Nature 317 (1985), 359–361). However, if these surface antigens of the tumour cells only differ slightly from the corresponding antigens of healthy cells, the immune system may possibly form no cytotoxically active T lymphocytes which could eliminate the tumour cells.

Therefore attempts have already been made to induce a cellular immune resistance against such tumour cells. For this it was firstly attempted to achieve an active immunization with unspecific immunostimulants such as Bacillus Calmette-Guerin (BCG), Corynebacterium parvum or vaccines from tumour cell extracts (Terry and Rosenberg eds., Immunotherapy of Human Cancer (1982), Elsevier North Holland). Better results were obtained using the concept of so-called adoptive immunotherapy. In this case lymphocytes of the patient are activated in vitro and then re-implanted. The in vitro activation to form such "promiscuous killer cells" (D. Thiele et al., Immunology Today 10 (1989), 375–381) is usually carried out by addition of interleukin 2. The cytotoxic lymphocytes obtained are then denoted lymphokine-activated killer cells (LAK cells) (Rosenberg, Immunology Today 9 (1988), 58–62). In contrast to cytotoxic T lymphocytes, the action of LAK cells against tumour cells does not depend on a correct expression of the MHC genes for the recognition of tumour antigens and in contrast to the natural killer cells of the immune system LAK cells are also effective against fresh tumour cells. It has even already been possible to achieve the first clinical successes using LAK cells. However, a disadvantage of this form of adoptive immunotherapy are side-effects of interleukin 2 which is required in relatively high doses over a longer time period. This results primarily in an increase in the permeability of the capillaries and concomitant functional disorders of the organs (Rosenberg, Immunology Today 9 (1988), 58–62, Rosenstein et al., Journal Immunology 137 (1986), 1735–1742 and Ettinghausen et al., Surg. Forum 37 (1987), 388–389). In addition such LAK cells are obtained which when stimulated with interleukin 2, are directed against healthy endogenous cells (B. Chen et al., Cell. Immunol. 118 (1989), 458–469).

In the search for more effective methods for adoptive immunotherapy the lymphocytes to be activated were also cultured in the presence of autologous tumour cells (mixed lymphocyte tumor cultures, G. Fossati et al., International Journal of Cancer 42 (1988), 239–245; G. Degiovanni et al., Eur. J. Immunol. 18 (1988), 671–676; Wölfel et al., J. Exp. Med. 170 (1989), 797–819; Darrow et al., J. Immunol. 142 (1989), 3329–3335 and Notter et al., Int. J. Cancer 45 (1990), 834–841). In addition a method for the proliferation of tumour-infiltrating lymphocytes (TIL) in vitro has also been described (Yron et al., J. Immunol. 125 (1980), 238–245) in contrast to LAK cells, these tumour-infiltrating lymphocytes have a high tumour specificity i.e. they are only active against the tumour from which they themselves were isolated. Such tumour-infiltrating lymphocytes are not even effective against the same type of tumours from other patients. This significantly limits their therapeutic applicability.

SUMMARY OF THE INVENTION

The object of the present invention was therefore to provide tumoricidal T lymphocytes which are more suitable for tumour therapy than the previously known in vitro activated T lymphocytes.

This object is achieved by a mammalian cell line or active subcellular fractions thereof which are characterized in that a) when they are co-cultured with lymphocytes during which allogenic stimulation is avoided they activate lymphocytes to form tumoricidal T cells without the need to add mitogens or growth factors such as e.g. interleukin 2 and b) the lymphocytes activated in this way proliferate in their presence without addition of interleukin 2.

Surprisingly it turned out that tumoricidal T lymphocytes with a broad tumoricidal activity without HLA restriction can be obtained from lymphocytes by co-culture with a cell line according to the present invention or active subcellular fractions/fragments thereof. In this connection tumoricidal activity is understood as a killing effect and in particular a lytic effect on the respective tumour cells as well as an inhibitory action on the proliferation of these tumour cells.

A cell line is understood as those cells which have the capability of unlimited proliferation such as is characteristic of HeLa cells (ATCC CCL 2) (James D. Watson et al., Molecular Biology of the Gene, 4th edition, The Benjamin/Cummings Publishing Co., Inc. (1987), p. 963). Such cell lines are for example obtained by immortalizing human blood lymphocytes. Immortalization is preferably carried out by fusion with cytoplasts from the mouse myeloma cell line Ag8.653 according to the method described in EP-B 0 093 436 or in EP-B 0 256 512 (the content of which is also subject matter of the present patent application). The immortalized lymphocyte lines thus obtained are then co-cultured with human donor lymphocytes.

Blood lymphocytes are preferably used as lymphocytes. However, it is also possible to use tumour-infiltrating lymphocytes (TIL) as well as lymphocytes from the spleen or lymphatic nodes. In this connection it is preferable to purify the lymphocyte preparation before use. When using blood lymphocytes it is particularly expedient to substantially remove the erythrocytes and to concentrate the mononuclear cells. It is also advantageous to deplete the number of cells which can be allogenically stimulated by the cell line according to the invention or active fragments thereof.

In order to avoid allogenic stimulation, lymphocytes which are susceptible to such stimulation are eliminated from the donor lymphocyte population before co-culture. For this monocytes, macrophages, natural killer cells and MHC-restricted cytotoxic T cells, also especially those directed against allogenic MHC of the activator cell line and their precursor cells are preferably eliminated by incubation with L-leucyl-L-leucine methyl ester according to Thiele and Lipsky (The Journal of Immunology, Vol. 136, No. 3 (1986), p. 1038–1048). Those immortalized lymphocyte lines are selected after the co-culture which cause an activation of the donor lymphocytes to form tumoricidal T lymphocytes during this co-culture. In this process those activating lymphocyte lines which are lysed by the donor lymphocytes which activate them during the co-culture are preferably examined further. For the further selection, these activating lymphocyte lines are cultured together with the donor lymphocytes which are activated by them and a series of different tumour cell lines. Finally those activating lymphocyte lines are selected which lead to activated donor lymphocytes with tumoricidal action against the examined tumour cell lines. In this case tumoricidal action is not only to be understood as the killing, in particular lysis, of the examined tumour cell lines but also an inhibitory effect on proliferation. This tumoricidal action can for example be detected by means of cytotoxicity tests familiar to a person skilled in the art, for example in that the tumour cell lines which can be distinguished morphologically from the tumoricidal T lymphocytes as well as from the activating lymphocyte line disappear from the co-culture or are at least overgrown by tumoricidal T lymphocytes during longer culture. The tumoricidal T lymphocytes are preferably $CD3^+$, $CD4^+$ and/or $CD8^+$.

A preferred subject matter of the present invention is a lymphocyte cell line, particularly preferably a B lymphocyte cell line, or active fragments thereof, which is characterized in that a) when they are co-cultured with lymphocytes in which allogenic stimulation is avoided they activate lymphocytes to form tumoricidal T cells without having to add mitogens or growth factors such as e.g. interleukin 2 and b) the lymphocytes activated in this way proliferate in their presence without addition of interleukin 2.

The human B cell lines HB 654 and HB 617 are especially preferred.

Using the cell lines and active fractions according to the present invention it is possible by simple co-culture with lymphocytes while avoiding allogenic stimulation to cause an activation of these lymphocytes to form tumoricidal T cells. This activation preferably takes place while the lymphocytes are in direct contact with the cell lines or active fractions (fragments) thereof. It has turned out that addition of antibody against IL2 and/or the IL2 receptor inhibits the activating effect of the cell lines according to the invention.

Therefore the present invention also concerns a process for the production of tumoricidal T lymphocytes by co-culturing lymphocytes with a cell line according to the present invention or active fragments thereof.

In order to carry out the process according to the present invention lymphocytes (preferably mononuclear lymphocytes) are firstly isolated from the blood or from tumours of a donor according to known methods e.g. by a Ficoll density gradient centrifugation. Subsequently the remaining lymphocytes are cultured in the usual lymphocyte culture medium together with a cell line according to the present invention or active fragments thereof, preferably the human B cell lines HB 654 and/or HB 617 under conditions which enable cell contact. In this process the cell line is preferably added to the lymphocytes in a deficit of 1:100. The culture is continued until the activation of tumoricidal T cells can be detected on the basis of the elimination of the activating cell line. A culture of about 8 days is usually necessary for this. An activation and proliferation of tumoricidal T lymphocytes is achieved by means of the co-culture according to the present invention without having to add growth factors or mitogens such as e.g. lymphokines, in particular interleukin 2. This is particularly important for the therapeutic use of the tumoricidal T lymphocytes obtained since such factors can produce side effects during the therapeutic application. However, a persistent proliferation of the tumoricidal T lymphocytes obtained requires the constant presence of the cell line according to the present invention or active fragments thereof and the possibility of forming cell—cell contacts. Since the tumoricidal activity of the activated lymphocytes obtained is also directed against the cell line according to the present invention, it is therefore necessary to continuously supply this cell line in order to achieve persistent proliferation. Although, without such an addition proliferation of tumoricidal T lymphocytes stagnates after one to two days, the tumoricidal T lymphocytes survive for three to four weeks during which they transform from blasts into very small cells which join together to form aggregates. They retain their tumoricidal activity and can again be converted into a proliferating state after a latency period of three to six days by addition of the cell line according to the present invention or active fragments thereof.

In addition to vital proliferable cells for co-culturing with the cell line according to the present invention it is also possible to use a cell line according to the present invention treated with mitomycin which has been lethally irradiated or chemically immobilized e.g. with formaldehyde or a subcellular fraction such as e.g. a membrane fraction, membrane vesicle or an extract from such a subcellular fraction. Furthermore the cell line according to the present invention can also be fused with other cells and the fusion cells obtained can be used for activation.

Therefore the present invention also concerns a process for the production of tumoricidal T lymphocytes by co-culturing lymphocytes from blood, during which allogenic stimulation is avoided, with a cell line according to the present invention, active derivatives or subcellular fractions of the cell line according to the invention or with fusion products of this cell line with other cells without adding mitogens or growth factors such as interleukin 2.

Since growth factors or mitogens do not have to be added in such a process for the production of cytotoxic T lymphocytes and interleukin 2 does not have to be added to the tumoricidal T lymphocytes obtained in order to continue their proliferation, they are better suited for an application in tumour therapy than the previously known promiscuous killer cells such as e.g. LAK cells. Due to their broader tumoricidal activity they are better suited for therapeutic application than tumour-infiltrating lymphocytes. In contrast to natural killer cells the tumoricidal cells produced according to the process according to the present invention are T cells.

The present invention therefore also concerns tumoricidal T lymphocytes having a broad tumoricidal activity which are characterized in that a) they have a tumoricidal effect on the tumour cell lines MOLT-4, Jurkat, THP-1, HL-60, HeLa, K-562, Malme-3M and Y79 and b) no interleukin 2 is detectable in the culture supernatant of these tumoricidal T lymphocytes during proliferation of these cells in the presence of the cell line HB 654 or HB 617 at a detection limit of 0.5 IU/ml.

The tumoricidal T lymphocytes according to the present invention are thus obtainable by simply co-culturing lymphocytes with a cell line according to the present invention or active derivatives or subcellular fractions of this cell line on a fusion product of this cell line with another cell until the activation of lymphocytes to tumoricidal T cells is detectable e.g. by means of the elimination of the activating cell line. Surprisingly it turned out that the tumoricidal T lymphocytes obtained in this way have a tumoricidal action on a multitude of tumour cell lines such as e.g. MOLT-4, Jurkat, THP-1, HL-60, HeLa, K-562, Malme-3M and Y79. A further distinguishing feature of these tumoricidal T lymphocytes is that interleukin 2 cannot be detected in their culture supernatant neither during the activation nor during subsequent proliferation of the activated cells (IL2 ELISA; DuPont, Catalogue No. NEK-057; lower detection limit 0.5 IU/ml).

As already stated human tumoricidal T lymphocytes are obtainable using the activating cell line according to the present invention without having to add mitogens or growth factors such as lymphokines, in particular interleukin 2, which can lead to side effects during therapy. Thus the present invention also concerns the use of tumoricidal T lymphocytes according to the present invention for the production of a therapeutic agent which can be used in tumour therapy. For such a therapeutic application the tumoricidal T lymphocytes according to the present invention are washed according to methods known to a person skilled in the art (e.g. by centrifugation and resuspension of the pellet in physiological saline which is repeated several times e.g. three times), they are isolated if desired and taken up in a medium suitable for the administration (e.g. physiological saline).

In addition to this ex vivo activation of lymphocytes to tumoricidal T lymphocytes, lymphocytes can also be activated in vivo to tumoricidal T lymphocytes by administration of an activating cell line according to the present invention or derivatives or subcellular fractions of this cell line. The activating cell line is washed according to methods known to a person skilled in the art for such a therapeutic application and taken up in a medium suitable for the administration such as e.g. physiological saline.

Therefore the present invention in addition concerns the use of an activating cell line according to the present invention or an active subcellular fraction (fragments) or appropriate derivative of this cell line which induces lymphocytes to form tumoricidal T cells for the production of a therapeutic agent which is applicable in tumour therapy.

The active subcellular fractions are particularly suitable for a direct in vivo application. These fractions can be used to directly activate lymphocytes in the body to tumoricidal T lymphocytes. It is particularly advantageous to apply these fractions directly to the tumour in order to activate tumour-infiltrating lymphocytes to tumoricidal T lymphocytes.

An active subcellular fraction is understood as a fraction of a cell line according to the invention which induces lymphocytes to form tumoricidal T cells in an analogous manner to the cell lines according to the invention (e.g. HB 617 and HB 654). Such fractions can for example be subcellular vesicles that are obtained by hypotonic shock or cell-free membrane vesicles that are obtained by incubation with Cytochalasin B. An eluate from the cell lines according to the invention that can for example be obtained after incubation with sodium chloride and sodium citrate is also suitable. Such fractions of the cell lines according to the invention can be purified further by methods familiar to a person skilled in the art, for example by chromatographic purification during which the activity of the fraction (the property of forming tumoricidal T lymphocytes) has to be checked after each purification step.

The invention therefore also concerns a process for producing an active fraction from lymphocyte cell lines which
a) activates lymphocytes to tumoricidal T cells in a co-culture with lymphocytes in which an allogenic stimulation is avoided without having to add mitogens or growth factors and
b) the lymphocytes activated in this manner proliferate in its presence without the addition of interleukin 2
which is characterized in that a mammalian cell line which has these properties
(i) is fractionated
(ii) the fractions are separated and it is examined whether these fractions activate lymphocytes to tumoricidal T cells in an analogous manner to the initial cell line,
(iii) such an active fraction is selected and is further fractionated and isolated while checking its activity until the desired degree of purity has been reached.

The tumoricidal T lymphocytes can also be used ex vivo to eliminate tumour cells in a cell preparation. This can preferably be used to eliminate (purging) tumour cells from stem cell isolates (e.g. bone marrow stem cells) by co-culture with tumoricidal T lymphocytes or a lymphocyte cell line according to the invention. The stem cells purified in this manner can for example again be implanted in the patient after radiation or chemotherapy (autologous bone marrow transplantation).

Finally, the corresponding therapeutic compositions are also a subject matter of the present invention which contain tumoricidal T lymphocytes according to the present invention or an activating cell line according to the present invention or a subcellular fraction or corresponding derivative of this cell line which induces lymphocytes to form tumoricidal T cells, in each case together with the usual pharmaceutical carrier, filling and/or auxiliary agents.

The cell line HB 654 according to the invention was deposited on 24.03.1993 at the "Deutsche Sammlung für Zellkulturen und Mikroorganismen GmbH", Mascheroder Weg 1 b, D-3300 Braunschweig under the number DSM ACC 2122.

The cell line HB 617 according to the invention was deposited on 11.03.94 at the "Deutsche Sammlung für Zellkulturen und Mikroorganismen GmbH", Mascheroder Weg 1 b, D-3300 Braunschweig under the number DSM ACC 2166.

The present invention is elucidated further by the following examples.

BRIEF DESCRIPTION OF THE DRAWINGS

FIG. 2 shows the release of BrdU after stimulation with vesicles according to the invention as a measure of the killer activity of the lymphoblasts that are formed.

Figure 1:
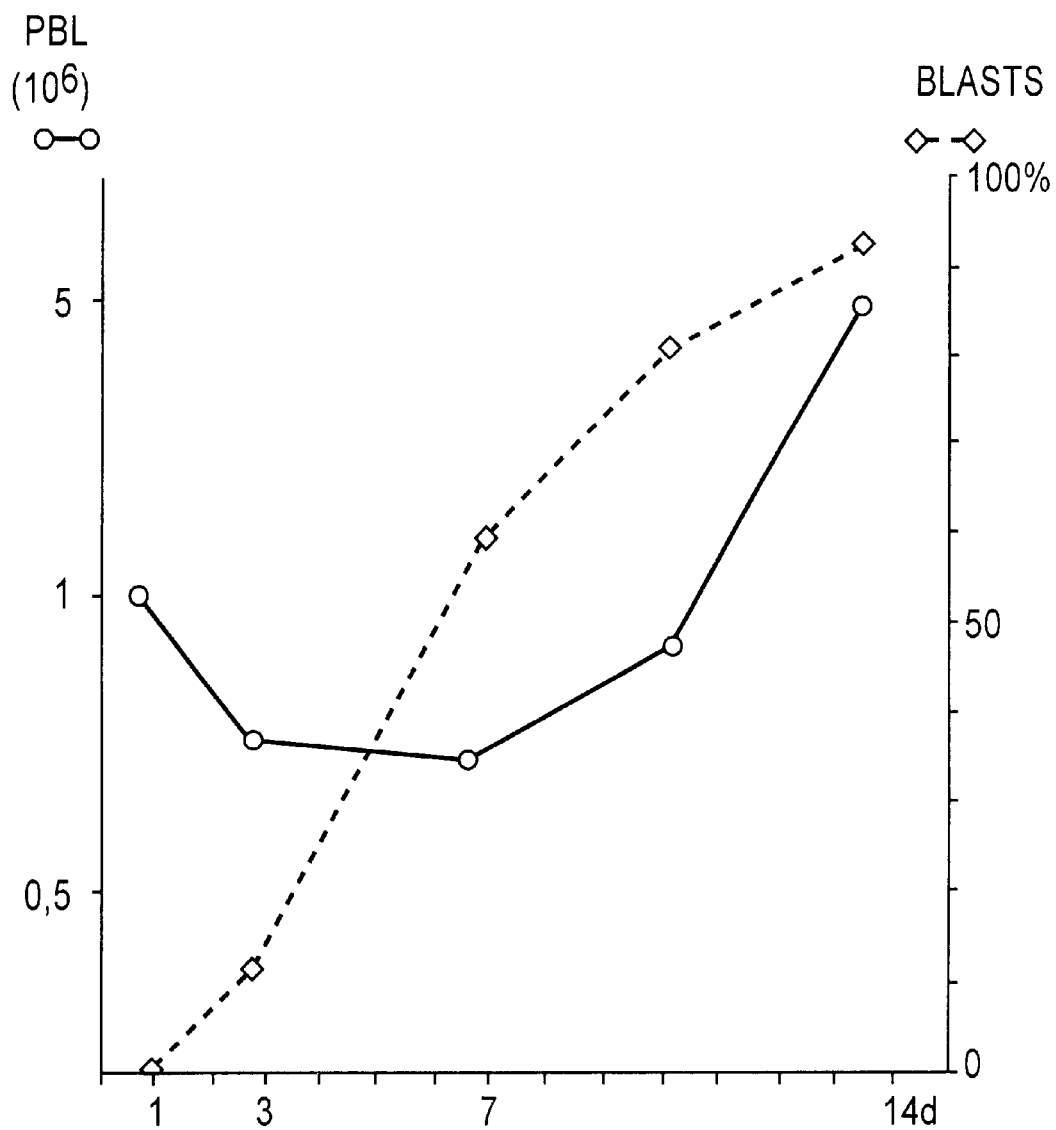
FIG. 1 shows the effect of vesicles according to the invention on the number of vital blood cells (PBL) and the formation of lymphoblasts (d:days).

Curve 1: stimulation with HB cells
Curve 2: stimulation with eluate
Curve 3: spontaneous release
Curve 4: blank value

DETAILED DESCRIPTION OF THE INVENTION

EXAMPLE 1

Production of a Cell Line which when Co-Cultured with Lymphocytes while Avoiding Allogenic Stimulation Leads to Induction of Lymphocytes to Form Tumoricidal T Cells The production of an activator cell line according to the present invention is carried out by immortalization of lymphocytes according to the method described in EP-B 0 093 436. For this human peripheral blood lymphocytes are firstly isolated by Ficoll gradient centrifugation. Cytoplasts from the mouse myeloma cell line P3X63 Ag8.653 (ATCC CRL1580) are produced by treatment with cytochalasin B as described in EP-B 0 093 436. $1 \times 10^7$ of the human peripheral blood lymphocytes are mixed each time with $1 \times 10^7$ cytoplasts of the myeloma cell line Ag8.653 and sedimented by centrifugation. The supernatant liquid is carefully removed. 0.8 ml 50% polyethylene glycol 4000 solution is added at a slow constant rate over a period of 1 min while shaking gently and continuously. Subsequently 5 ml Dulbecco's minimal essential medium (DMEM) is added at room temperature over a time period of 5 min. After addition of a further 20 ml DMEM, the cells are sedimented, resuspended in 5 ml fresh DMEM complete medium and distributed in the wells of a cell culture plate coated with murine macrophages from the abdominal cavity as feeder cells. The individual cultures are then fed with DMEM complete medium at intervals of two to three days. Finally the clone is selected which can activate lymphocytes to form T lymphocytes. For this peripheral blood lymphocytes are firstly incubated with L-leucyl-L-leucine methyl ester as described in example 2 in order to eliminate cells which can be activated by allogenic stimulation to form tumoricidal T cells. The lymphocyte population obtained in this way is then co-cultured with the immortalized lymphocyte cell line to be tested under conditions which enable direct cell—cell contact. Those immortalized lymphocyte cell lines which are lysed during such a co-culture by the tumoricidal T lymphocytes that are activated by them are examined further. For this these selected cell lines are cultured together with the tumoricidal T lymphocytes that are activated by them as well as with various tumour cell lines. Finally, those immortalized activating lymphocyte cell lines are selected which during this process produce T lymphocytes with a tumoricidal effect on various tumour cell lines. This tumoricidal action is detected by the fact that the tumour cell lines which are morphologically distinguishable from the tumoricidal T lymphocytes as well as from the activating lymphocyte cell lines disappear from the culture during this co-culture or at least decrease in numbers compared to an untreated control culture. The cell line HB 654 was obtained in this way.

Permanent human B lymphocyte lines which had been immortalized by infection with the Epstein-Barr virus were examined for activator properties using the same procedure. Twenty different EBV-positive B lines cloned by single cell culture are tested in a co-culture with blood lymphocytes which are pre-treated with leucyl-leucine methyl ester. The seeding density of the blood lymphocytes is $2 \times 10^6$ per ml culture medium (Iscove mod. DMEM+15% FCS; BM). 50-, 100- and 200-fold fewer cells of each of the B lines are added to the blood lymphocytes in separate preparations and incubated at 37° C. in a 5% $CO_2$ atmosphere. The cell line HB 617 was obtained in this manner which also has an action according to the invention.

EXAMPLE 2

Production of Tumoricidal T Lymphocytes by Co-Culture with the Human B Cell Line HB 654

The mononuclear cells are isolated from human peripheral blood in the usual way by Ficoll® gradient centrifugation. In order to eliminate monocytes, macrophages, natural killer cells and MHC-restricted cytotoxic T cells, in particular those directed against allogenic MHC of the activating cell line HB 654, and their precursors, the mononuclear cells obtained are incubated for 15 min at room temperature in PBS containing 250 μmol/l L-leucyl-L-leucine methyl ester according to Thiele and Lipsky (The Journal of Immunology, Vol. 136, No. 3 (1986), p. 1038–1048). Subsequently the cells are taken up in Iscove's modified Dulbecco's medium with 15% FCS and, after adding a deficit (ca. 1:10) of HB 654 cells, they are incubated for 6 to 8 days at 37° C. until tumoricidal T lymphocytes can be detected on the basis of their eliminating activity on the activator cell line.

EXAMPLE 3

Effect of Tumoricidal T Lymphocytes

The tumoricidal T lymphocytes obtained according to example 2 each from 20 different donors are added to cultures of human tumour lines (see tables I and II). The tumoricidal effect on these tumour cells is monitored under a microscope. The growth of these various tumour cell lines is inhibited or they are killed by the tumoricidal T lymphocytes according to the present invention.

TABLE I

| Human tumour line | Tumour cell density | E/T[1] | Surviving tumour cells (% of control)[2] | Growth of tumour cells[3] | Source |
|---|---|---|---|---|---|
| MOLT 4 | $1 \times 10^5$/ml | 4/1 | 0 | no | ATCC CRL 1582 |
| JURKAT | $1 \times 10^5$/ml | 2/1 | 0 | no | ATCC TIB 152 |
| THP-1 | $5 \times 10^4$/ml | 4/1 | <5 | yes[5] | ATCC TIB 202 |
| HL-60 | $5 \times 10^4$/ml | 10/1 | <15 | yes[6] | ATCC CCL 240 |
| HELA | $1 \times 10^3$/cm2 | 10/1 | <5 | yes[7] | ATCC CCL 240 |
| K562 | $1 \times 10^5$/ml | 5/1 | ca. 40[4] | yes[8] | ATCC CCL 243 |
| MALME 3M | $2 \times 10^3$/cm2 | 10/1 | <5 | no | ATCC HTB 64 |
| Y79 | $2 \times 10^3$/cm2 | 10/1 | <5 | no | ATCC HTB 18 |

[1]effector/tumour cell ratio
[2]microscopic evaluation after 48 hours
[3]after a 14 day culture
[4]growth inhibition
[5]ca. 2 colonies per $5 \times 10^4$ THP-1 cells
[6]ca. 10 colonies per $5 \times 10^4$ HL-60 cells
[7]4 colonies per $2.5 \times 10^4$ HELA cells
[8]elimination of growth inhibition after 3 days

TABLE II

| Human tumour line | Type of tumour |
|---|---|
| MOLT 4 | acute lymphoblastic leukemia |
| Jurkat | acute T cell leukaemia |
| THP-1 | acute monocytic leukaemia |
| HL-60 | promyelocytic leukaemia |
| HeLa | cervical carcinoma |
| K-562 | chronic myelogenic leukaemia |
| Malme-3M | malignant melanoma |
| Y79 | retinoblastoma |

EXAMPLE 4

Production of Tumoricidal T Lymphocytes (Killer T Cells) by means of Cell-Free Membrane Vesicles Which are Produced from HB 654 Cells by Treatment with Cytochalasin B A. Production of Membrane Vesicles:

HB 654 cells are also induced to tie off membrane vesicles ("blebs") using the method described by MAUL, G. D. (in: Techniques in Somatic Cell Genetics, Ed. J. W. SHAY; Plenum Press, New York, 1982) by incubation with Cytochalasin B (CB, Aldrich Biochemicals) which can be separated by allowing shearing forces to act on the cells (without cell destruction).

HB 654 cells from cultures in a logarithmic growth phase are washed twice in serum-free culture medium (RPMI 1640, BM), suspended in this medium at a density of ca. $2\times10^7$ cells/ml and heated to 37° C. CB (stock solution: 5 mg/ml DMSO) is added (final concentration: 25 μg/ml). The suspension is incubated for one minute at 37° C. and then rotated for one minute on a vortex apparatus. The cells are suspended by low speed centrifugation. The supernatant containing vesicles is filtered through a 5 μm filter. On average a yield of 3 membrane vesicles is obtained from one HB 654 cell.

B. Production of Tumoricidal Killer T Cells from Blood Lymphocytes:

Mononuclear blood cells are isolated as described in example 2 by gradient centrifugation, treated with leucyl-leucine methyl ester and incubated at a density of ca. $2\times10^6$ cells/ml of a culture medium (Iscove mod. DMEM plus 15% FCS) to which ca. $2\times10^6$ vesicles had been added per ml. The cells are supplied with fresh culture medium on day 7 and 10 which in turn contains $2\times10^6$ vesicles per ml. On days 3, 7, 10 and 13 the total number of vital blood cells (PBL) and the proportion of lymphoblasts in the culture are determined (FIG. 1). The determination showed that the number of living blood cells decreases at first and then increases on day 7. On day 13 the number of vital cells is approximately 5-fold the number of originally sown cells. The proportion of lymphoblasts increases from 0% on day 1 of the culture to ca. 95% on day 13.

C. Effect of Lymphoblasts Induced with Vesicles on Tumour Cells:

The tumoricidal function towards the tumour lines Jurkat, THP-1 and HB654 of the lymphoblasts obtained according to B. is examined on day 14 after setting up the culture. The destruction of the tumour cells is measured using the "Cellular DNA fragmentation ELISA kit" (Boehringer Mannheim GmbH, GER, Order No. 1585045) according to the manufacturer's instructions.

Principle: Tumour (target) cells are labelled metabolically by addition of 5-bromo-2' deoxy-uridine (BrdU) to the culture medium. Proliferating cells incorporate BrdU into the DNA instead of thymidine. Cytotoxic effects on these target cells can then be measured based on the release of BrdU-labelled DNA by means of an ELISA (enzyme-linked immunosorbent assay) in which anti-DNA antibodies bound to the wall and an anti-BrdU antibody-peroxidase conjugate are used.

After a 24 hour co-culture with the lymphoblasts according to B. at least 80% of the tumour cell DNA which can be maximally released is found in the culture supernatant in all three tumour lines at an effector/target ratio of 4/1 and of 100% at an E/T ratio of 10/1.

EXAMPLE 5

Production of Killer T Cells by Subcellular Vesicles Which Have Been Obtained in a Physical Manner by Hypotonic Shock A method modified according to Jett et al., (Jett et al., J. Biol. Chem. 252 (1977), 2134–2142) was used as a further method of isolating subcellular fragments which are suitable for producing the claimed effect. The vesicles were obtained as follows:

Cells of the stimulator cell line HB 654 were washed in Earls buffer (containing 0.9 mM calcium chloride and 0.5 mM magnesium chloride in PBS buffer) and subsequently taken up in the same buffer in 1% of the original culture volume. In order to produce the vesicles, 90% glycerol was added to this at a final concentration of 30% in three steps at 5 minute intervals. The cells loaded with glycerol were centrifuged (1200×g for 10 minutes, 4° C.) and the supernatant was discarded. Lysis buffer (ca. 1% of the original culture volume; 10 mM Tris/HCl, pH 7.4, 1 mM $MgCl_2$, 1 mM $CaCl_2$) was added to the cell sediment while mixing vigorously and incubated for 5 min in ice water. This was followed by several centrifugation steps in which cell debris was removed and the vesicle fraction concentrated. A first centrifugation was carried out at 700×g for 10 min. The supernatant was subjected to a second centrifugation at 700×g for 10 min, the precipitate was discarded. The precipitate of the second centrifugation was also discarded and the centrifugation was carried out again. The precipitate was again discarded and the remaining supernatant was subjected to a centrifugation at 2300×g for 10 min. This supernatant was used to bring the vesicles into the precipitate in a last centrifugation of 4500×g for 10 min. The suspended precipitate was filtered once again through a 5 μm filter and used subsequently. In order to examine the stimulating property of the vesicles obtained in this manner, these were used in a stimulation preparation which was carried out as described above. For this vesicles were obtained from $1\times10^8$ HB 654 cells as described above, these were subsequently used to condition peripheral blood lymphocytes ($2\times10^7$ cells after treatment with leucyl-leucine methyl ester). The procedure was exactly the same as described in examples 2 and 3.

In order to evaluate the results, a test for "kill activity" was carried out. This test was carried out as described in example 3. In this procedure the killer T cells produced in the above manner were used as effector cells and the T cell tumour line MOLT 4 was used as the target cell. In order to quantify the lysis rate of the target cells, the "Cellular DNA Fragmentation ELISA-Kit" from Boehringer Mannheim GmbH was used for this. The procedure was as stated in example 4. The result of the test is given in FIG. 2. It turned out that the blasts formed by the vesicles had killer T cell activity.

The blank value described in FIG. 2 corresponds to an absorbance of the reagent without addition of cells. The measured value for spontaneous release corresponds to an absorbance which was obtained when target cells were added without effector cells.

EXAMPLE 6

Production of Killer T Cells by an Eluate from the Stimulator Cell Line which is Produced by Incubation with a Suitable Buffer A method described in the following was used as a further method to obtain subcellular fragments which are suitable for producing the claimed effect.

Cells of the stimulator cell line HB 654 which had been cultured according to the methods stated in the other examples were washed three times in Hanks Balanced Salt Solution (HB SS, Boehringer Mannheim GmbH, GER) and subsequently taken up in 150 mmol/l NaCl, 15 mmol/l Na-citrate, pH 7.2 at a density of about $2\times10^7$ cells/ml. They were subsequently incubated for 30 min at 37° C. Afterwards the cells were sedimented by a centrifugation for 7 min at 4500×g.

The supernatant obtained in this manner represents the eluate. The supernatant is filtered once again through a 5 μm filter and used subsequently. In order to examine the stimulating property of the eluate obtained in this manner, this was used in a stimulation preparation which was carried out as described above. For this eluate was obtained as described above from $2\times10^7$ HB 654 cells, and this was used subsequently to condition peripheral blood lymphocytes ($2\times10^7$ cells). The procedure was as described in the previous example.

A test for "kill activity" was carried out to evaluate the results. This test was carried out as described in the previous examples. For this the killer T cells produced in the above manner were used as effector cells and Jurkat as the target cell. In order to quantify the lysis rate of the target cells, the "Cellular DNA Fragmentation ELISA-Kit" from Boehringer Mannheim GmbH was used for this. The procedure was as stated in example 4. It turned out that the blasts formed by the eluate had killer T cell activity. Absorbances for BrdU release (after subtracting the absorbance for spontaneous release) of 0.121, 0.214, 0.269 and 0.114 were obtained with four different vesicle preparations.

What is claimed is:

1. Activated lymphocytes obtained by a lymphocyte activing process, which have a killing, lysing or proliferation inhibiting activity in vitro towards each one of the tumor cells selected from the group consisting of MOLT-4 (ATTC CRL 1582), Jurkat (ATCC TIB 152), THP-1 (ATCC TIB 202), HL-60 (ATCC CCL 240), HeLa (ATCC CCL 2), K-562 (ATCC CCL 243), Malme-3M (ATCC HTB 64) and Y79 (ATCC HTB 18), wherein said activity is not MHC restricted and wherein said activated lymphocytes are T lymphocytes that bear a CD3 and at least one of CD4 or CD8 surface antigens and that proliferate in the presence of an activating agent without addition of a growth factor or a mitogen, which activating agent is,
   a) a mammalian activator cell line that is effective in generating activated lymphocytes from the donor lymphocytes, the cell line being DSM ACC 2122 (HB 654) or DSM ACC 2166 (HB 617); or
   b) a subcellular vesicle fraction of said activator cell line, wherein the fraction is effective in generating activated lymphocytes from the donor lymphocytes; or
   c) an extract of said cell line, wherein the extract is effective in generating activated lymphocytes from the donor lymphocytes,
   wherein said activated lymphocytes are obtained by a process wherein donor lymphocytes selected from the group consisting of blood lymphocytes, tumor infiltrating lymphocytes, spleen lymphocytes, and lymph node lymphocytes are incubated in a suitable lymphocyte culture medium in the presence of said activating agent, and
   without the addition of mitogens or growth factors, and wherein no interleukin 2 is detectable at a detection limit of 0.5 IU/ml in a supernatant obtained therefrom during proliferation of the cells, and wherein after said incubation said activated lymphocytes are present in said lymphocyte culture medium.

2. The activated lymphocytes according to claim 1, wherein the subcellular vesicle fraction is produced by subjecting said mammalian activator cell line to a hypotonic shock or a treatment with Cytochalasin B.

3. The activated lymphocytes according to claim 1, wherein the extract comprises a supernatant of a suspension of said mammalian cell line after incubation in the presence of NaCl and Na-citrate.

4. The activated lymphocytes according to claim 1, wherein prior to incubation the donor lymphocytes are purified by eliminating cells that are susceptible to allogeneic stimulation.

5. The activated lymphocytes according to claim 4, wherein said cells that are susceptible to allogeneic stimulation are selected from the group consisting of monocytes, macrophages, natural killer cells, and MHC restricted cytotoxic T cells.

6. The activated lymphocytes according to claim 4, wherein the donor lymphocytes are purified by incubation with L-Ieucyl-L-leucine methylester.

7. A pharmaceutical composition effective in killing, lysing or inhibiting proliferation of different tumor cells in vitro, wherein the tumor cells comprise MOLT-4 (ATCC CRL 1582), Jurkat (ATOC TIB 152), THP-1 (ATOC TIB 202), HL-60 (ATOC CCL 240), HeLa (ATCC CCL 2), K-562 (ATCC CCL 243), Malme-3M (ATCC HTB 64) and Y79 (ATCC HTB 18), wherein the composition comprises activated lymphocytes according to claim 1 and a pharmaceutically acceptable carrier.

8. A pharmaceutical composition for generating, in vitro, activated lymphocytes comprising an activation agent which is
   a) a mammalian activator cell line that is effective in generating activated lymphocytes from donor lymphocytes, said cell line being DSM ACC 2122 (HB 654) or OSM ACC 2166 (HB617); or
   b) a subcellular vesicle fraction of said activator cell line, wherein the fraction is effective in generating activated lymphocytes from the donor lymphocytes; or
   c) an extract of said activator cell line, wherein the extract is effective in generating activated lymphocytes from the donor lymphocytes, and a pharmaceutically acceptable carrier.

9. A process for killing, lysing or inhibiting proliferation of tumor cells in vitro, wherein the tumor cells are from a tumor selected from the group consisting of acute lymphoblastic leukemia, acute T cell leukemia, acute monocytic leukemia, promyelocytic leukemia, cervical carcinoma, chronic myelogenic leukemia, malignant melanoma, and retinoblastoma, the process comprising contacting said tumor cells the activated lymphocytes of claim 1 without addition of growth factor or mitogen.

10. Isolated activated lymphocytes, which have a killing, lysing or proliferation inhibiting activity in vitro towards each one of the tumor cells selected from the group consisting of MOLT-4 (ATCC CRL 1582), Jurkat (ATCC TIB 152), TH-1 (ATCC TIB 202), NL-60 (ATOC CCL 240), HeLa (ATCC CCL 2), K-562 (ATOC CCL 243), Malme-3M (ATCC HTB 64) and Y79 (ATCC HTB 18), wherein said activity is not MHC restricted and wherein said activated lymphocytes are T lymphocytes that bear a CD3 and at least one of CD4 and CD8 surface antigens, and that proliferate in the presence of an activating agent without addition of a growth factor or a mitogen, which activating agent is
   a) a mammalian activator cell line that is effective in generating activated lymphocytes from donor lymphocytes, said cell line being DSM ACC 2122 (HB 654) or DSM ACC 2166 (HB617);
   b) a subcellular vesicle fraction of said activator cell line, wherein the fraction is effective in generating activated lymphocytes from the donor lymphocytes; or
   c) an extract of said activator cell line, wherein the extract is effective in gene rating activated lymphocytes from the donor lymphocytes.

11. A pharmaceutical composition effective for killing, lysing or inhibiting proliferation in vitro of each one of the tumor cells selected from the group of MOLt-4 (ATCC CRL 1582), Jurkat (ATCC TIB 152), THP-1 (ATCC TIB 202), HL-60 (ATCC CCL 240), HeLa (ATCC CCL 2), K-562 (ATCC CCL 243), Malme-3M (ATCC HTB 64) and Y79 (ATCC HTB 18), wherein the composition comprises the activated lymphocytes defined in claim 10, and a pharmaceutically acceptable carrier.

12. A process for killing, lysing or inhibiting proliferation of tumor cells vitro wherein the tumor cells are from a tumor selected from the group consisting of acute lymphoblastic leukemia, acute T cell leukemia, acute monocytic leukemia, promyelocytic leukemia, cervical carcinoma, chronic myelogenic leukemia, malignant melanoma, and retinoblastoma, the process comprising contacting said tumor cells with the activated lymphocytes according to claim 10, without addition of an exogenous growth factor or mitogen.

* * * * *